US012680975B2

(12) United States Patent
De Oliveira Filho et al.

(10) Patent No.: US 12,680,975 B2
(45) Date of Patent: Jul. 14, 2026

(54) SMALL-SIZED, RECONFIGURABLE, MULTI-MEASUREMENT POTENTIOSTAT CIRCUITRY AND METHOD

(71) Applicant: KING ABDULLAH UNIVERSITY OF SCIENCE AND TECHNOLOGY, Thuwal (SA)

(72) Inventors: José Ilton De Oliveira Filho, Thuwal (SA); Khaled Nabil Salama, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 209 days.

(21) Appl. No.: 18/685,558

(22) PCT Filed: Aug. 1, 2022

(86) PCT No.: PCT/IB2022/057129
§ 371 (c)(1),
(2) Date: Feb. 22, 2024

(87) PCT Pub. No.: WO2023/026117
PCT Pub. Date: Mar. 2, 2023

(65) Prior Publication Data
US 2024/0353362 A1 Oct. 24, 2024

Related U.S. Application Data

(60) Provisional application No. 63/235,936, filed on Aug. 23, 2021.

(51) Int. Cl.
*G01N 27/02* (2006.01)
*G01N 27/48* (2006.01)
*G01N 33/49* (2006.01)

(52) U.S. Cl.
CPC ............. *G01N 27/02* (2013.01); *G01N 33/49* (2013.01); *G01N 27/48* (2013.01)

(58) Field of Classification Search
CPC ........ G01N 27/02; G01N 33/49; G01N 27/48; G01R 31/3183
(Continued)

(56) References Cited

U.S. PATENT DOCUMENTS

| | | | |
|---|---|---|---|
| 2004/0069625 A1* | 4/2004 | Desai | G01N 27/4045 204/400 |
| 2005/0016847 A1* | 1/2005 | Buehler | G01N 27/4035 204/406 |

(Continued)

OTHER PUBLICATIONS

Beduk, T., et al., "Rapid Point-of-Care COVID-19 Diagnosis with a Gold-Nanoarchitecture-Assisted Laser-Scribed Graphene Biosensor," Analytical Chemistry, Jun. 3, 2021, vol. 93, No. 24, pp. 8585-8594, ACS Publications.
(Continued)

*Primary Examiner* — Raul J Rios Russo
(74) *Attorney, Agent, or Firm* — PATENT PORTFOLIO BUILDERS PLLC

(57) ABSTRACT

Potentiostat circuitry for performing electrical tests on a biological material includes an integrated circuit having a processor; a power source configured to supply power to the integrated circuit; a reference electrode pad (RE) electrically connected to the integrated circuit and configured to electrically connect to a reference electrode of a sensor; a counter electrode pad (CE) electrically connected to the integrated circuit and configured to electrically connect to a counter electrode of the sensor; first to third working electrode pads electrically connected to the integrated circuit and configured to electrically connect to first to third working electrode of the sensor, respectively, and a communication module configured to exchange data and/or commands with
(Continued)

a smart device. The electrode pads are configured to measure a characteristic of the biological material.

20 Claims, 14 Drawing Sheets

(58) Field of Classification Search
USPC ......................................................... 324/650
See application file for complete search history.

(56) References Cited

U.S. PATENT DOCUMENTS

| | | | |
|---|---|---|---|
| 2007/0285099 A1 | 12/2007 | Lorimer et al. | |
| 2008/0073225 A1* | 3/2008 | Paulus ............... | G01N 33/5438 |
| | | | 205/792 |
| 2010/0224489 A1* | 9/2010 | Chapman ........... | G01N 27/4161 |
| | | | 204/286.1 |
| 2018/0259483 A1* | 9/2018 | Easley ................ | C12Q 1/6825 |
| 2018/0303386 A1 | 10/2018 | Hall et al. | |
| 2022/0229016 A1* | 7/2022 | Hogan ................ | G01N 27/413 |

OTHER PUBLICATIONS

Ghoreishizadeh, S., et al., "Sub-mW Reconfigurable Interface IC for Electrochemical Sensing," 2014, IEEE Biomedical Circuits and Systems Conference (BioCAS) Proceedings, Lausanne, Switzerland, Oct. 22-24, 2014, pp. 1-4, IEEE.

International Search Report in corresponding/related International Application No. PCT/IB2022/057129, date of mailing Oct. 26, 2022.

Rauf, S., et al., "Gold Nanostructure Laser-Scribed Graphene: A New Electrochemical Biosensing Platform for Potential Point-of-Care Testing of Disease Biomarkers," Biosensors and Bioelectronics, Feb. 27, 2021, vol. 180, 113116, pp. 1-8, Elsevier B.V.

Sun, A., et al., "A Multitechnique Reconfigurable Electrochemcial Biosensor for Integration into Mobile Technologies," 2015 IEEE Biomedical Circuits and Systems Conference (BioCAS), Atlanta, GA, USA, Oct. 22-24, 2015, pp. 1-4, IEEE.

Written Opinion of the International Searching Authority in corresponding/related International Application No. PCT/IB2022/057129, date of mailing Oct. 26, 2022.

* cited by examiner

| Measurement technique | Combinations | | |
|---|---|---|---|
| Liner Sweep Voltammetry | Φ + Π | Φ + Φ | ⊙ |
| Cyclic Voltammetry | Φ + Π | Φ + Φ | ⊙ |
| Differential Pulse Voltammetry | Φ + Π | Φ + Φ | ⊙ |
| Square Wave Voltammetry | Φ + Π | Φ + Φ | ⊙ |
| Normal Pulse Voltammetry | Φ + Π | Φ + Φ | ⊙ |
| Chronoamperometry | Φ + Π | Φ + Φ | ⊙ |
| Pulsed Amperometry Detection | Φ + Π | Φ + Φ | ⊙ |

FIG. 6

| | Bipolar | Unipolar | | |
|---|---|---|---|---|
| Voltage | ± 2V | +4V | | 3 pins setup |
| Current | ± 400μA | 800μA | | |
| | ± 100μA | ± 200μA | | 5 pins setup |

START APPLICATION — 1100

CONNECT CELL/SENSOR TO SMART PHONE — 1102

SELECT ONE OR MORE TEST TECHNIQUES TO BE PERFORMED — 1104

INSTRUCT USER WHICH ELECTRODE PADS TO CONNECT TO THE SELECTED CELL — 1106

MEASURE A CHARACTERISTIC OF A BIOLOGICAL MATERIAL — 1108

DISPLAY CHARACTERISTIC — 1110

SMALL-SIZED, RECONFIGURABLE, MULTI-MEASUREMENT POTENTIOSTAT CIRCUITRY AND METHOD

CROSS-REFERENCE TO RELATED APPLICATIONS

This application is a U.S. National Stage Application of International Application No. PCT/IB2022/057129, filed on Aug. 1, 2022, which claims priority to U.S. Provisional Patent Application No. 63/235,936, filed on Aug. 23, 2021, entitled "SMALL-SIZED RECONFIGURABLE MULTI-MEASUREMENT ELECTROCHEMICAL STATION FOR POINT OF CARE APPLICATIONS DEVICE," the disclosures of which is are incorporated herein by reference in their entirety.

BACKGROUND

Technical Field

Embodiments of the subject matter disclosed herein generally relate to a system that acts as a point of care for testing and is compatible with plural applications, and more particularly, to small, reconfigurable potentiostat circuitry that may be used at any location where the patient is present and can be reconfigured to interact with various tests performed at the patient's side.

Discussion of the Background

Many diseases can be detected today through point of care (POC) diagnostic devices that are configured to collect a patient's sample at her or his home, when visiting the doctor's office, at work, or even at large events taking place in mass venues. For example, it is common today for a patient to perform a blood glucose or pregnancy test at home. Today, more advanced bio- and chemo-sensors are produced in an effort to cover a large spectrum of the medical and biological tests that in the past could have been performed only within a lab. By liberating the patient from the fear of entering a lab, and the effort to get to that lab, the POC diagnostic devices allow a broad spectrum of patients to seek and obtain cheap and efficient medical care.

All these tests typically require a dedicated sensor or electrochemical cell to directly receive a signal or a body fluid or biological material from the patient and to perform one or more analysis steps on that signal or body fluid or biological material for extracting a characteristic of the patient, for example, the sugar level in the blood. That cell or sensor needs to be electrically connected to a readout circuitry, which is capable to apply a desired voltage to a working electrode and to extract the generated signal for determining the characteristic. For example, a typical 3 electrodes electrochemical cell 110 with an associated readout circuitry 120 is shown in FIG. 1 as system 100, and this system can be used for receiving a body fluid from the patient, e.g., blood, or saliva, or any other fluid or biological material, performing some testing, e.g., applying one or more voltages to the received biological material, and providing results of those measurements for further analysis.

The cell 110 has three electrodes, a reference electrode R, a counter electrode C, and a working electrode W. These electrodes extend on a substrate 112 and are configured to receive a biological material 114 for analysis. The cell 110 is configured to perform basic tests, like the blood glucose test. The electrodes of the cell 110 are configured to connected to corresponding electrodes of the readout circuitry 120. The three electrodes of the readout circuitry 120 include a reference electrode RE, a counter electrode CE, and a working electrode WE0. The working electrode WE0 is connected to a first operational amplifier 122. An input and the output of the operational amplifier 122 are connected to a variable resistor array 124. The output of the amplifier 122 is connected, through a first connecting device 126 to a sigma-delta analog to digital converter $$\Delta \sum\nolimits^+ - ADC$$

128 and another input of the amplifier 122 is connected to a first digital-to-analog converter 130. The reference electrode RE and the counter electrode CE are connected to an input of a second operational amplifier 140, through a second connection device 142. A second digital-to-analog converter DAC2 144 is connected to another input of the second amplifier 140. The counter electrode CE is also connected to the output of the second amplifier 140. The cell 110 is attached to the readout circuitry 120 as illustrated in the figure.

However, many other tests (e.g., cancer detecting test) that are being develop need more complicated reading out circuitry, which cannot be satisfied by the system 100, in order to be performed at the point of care. Some of the tests even require the simultaneous application of plural voltages, the need to use simultaneous sensors, or the simultaneous application of different techniques/measurements, which cannot be handled by the current system 100.

Thus, there is a need for a new system that is capable of performing multiple tests with different electrode/voltage configurations and sometimes to simultaneously provide such tests with plural sensors/cells. Also, there is a need that all these tests can be performed with a single, small platform so that the patient or the person that performs the tests does not have to carry and master different acquisition circuitry for these tests.

BRIEF SUMMARY OF THE INVENTION

According to an embodiment, there is a potentiostat circuitry for performing electrical tests on a biological material. The potentiostat circuitry includes an integrated circuit having a processor, a power source configured to supply power to the integrated circuit, a reference electrode pad electrically connected to the integrated circuit and configured to electrically connect to a reference electrode of a sensor, a counter electrode pad electrically connected to the integrated circuit and configured to electrically connect to a counter electrode of the sensor, a first working electrode pad electrically connected to the integrated circuit and configured to electrically connect to a first working electrode of the sensor, a second working electrode pad electrically connected to the integrated circuit and configured to electrically connect to a second working electrode of the sensor or to a first working electrode of another sensor, a third working electrode pad electrically connected to the integrated circuit and configured to electrically connect to a third working electrode of the sensor or to a second working electrode of the another sensor, and a communication module configured to exchange data and/or commands with a smart device. The reference electrode pad, the counter electrode pad, the first working electrode pad, the second working electrode pad and the third working electrode pad are configured to measure a characteristic of the biological material.

According to another embodiment, there is a point of contact testing device for determining a characteristic of a biological material. The point of contact testing device includes a sensor having a reference electrode, a counter electrode, and at least one working electrode, the sensor being configured to receive the biological material, and potentiostat circuitry. The potentiostat circuitry includes an integrated circuit having a processor, a reference electrode pad electrically connected to the integrated circuit and configured to electrically connect to the reference electrode of the sensor, a counter electrode pad electrically connected to the integrated circuit and configured to electrically connect to the counter electrode of the sensor, a first working electrode pad electrically connected to the integrated circuit and configured to electrically connect to the first working electrode of the sensor, a second working electrode pad electrically connected to the integrated circuit and configured to electrically connect to a second working electrode of the sensor or to a first working electrode of another sensor, a third working electrode pad electrically connected to the integrated circuit and configured to electrically connect to a third working electrode of the sensor or to a second working electrode of the another sensor, and a communication module configured to exchange data and/or commands with a smart device. The reference electrode pad, the counter electrode pad, the first working electrode pad, the second working electrode pad and the third working electrode pad are configured to measure the characteristic of the biological material.

BRIEF DESCRIPTION OF THE DRAWINGS

For a more complete understanding of the present invention, reference is now made to the following descriptions taken in conjunction with the accompanying drawings, in which:

FIG. 6 illustrates the various measurement techniques that are supported by the potentiostat circuitry of FIG. 2;

FIG. 8 illustrates the possible voltages and currents used by the potentiostat circuitry for various electrode/pin setups;

DETAILED DESCRIPTION OF THE INVENTION

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to potentiostat circuitry configured to work with a five-electrode cell or sensor. However, the embodiments to be discussed next are not limited to five electrodes, but may be applied to cells or sensors having less electrodes.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment, a novel potentiostat circuitry is designed to be small, reconfigurable for working with a variety of sensors or cells that include 3, 4, or 5 electrodes, to be powered by a USB or similar port, for example, from a smartphone, or to have its own power source, and to simultaneously read, if necessary, three different working electrodes and to apply two different electrochemistry techniques at the same time. This novel potentiostat circuitry is now discussed in more detail with regard to the figures.

Figure 1:
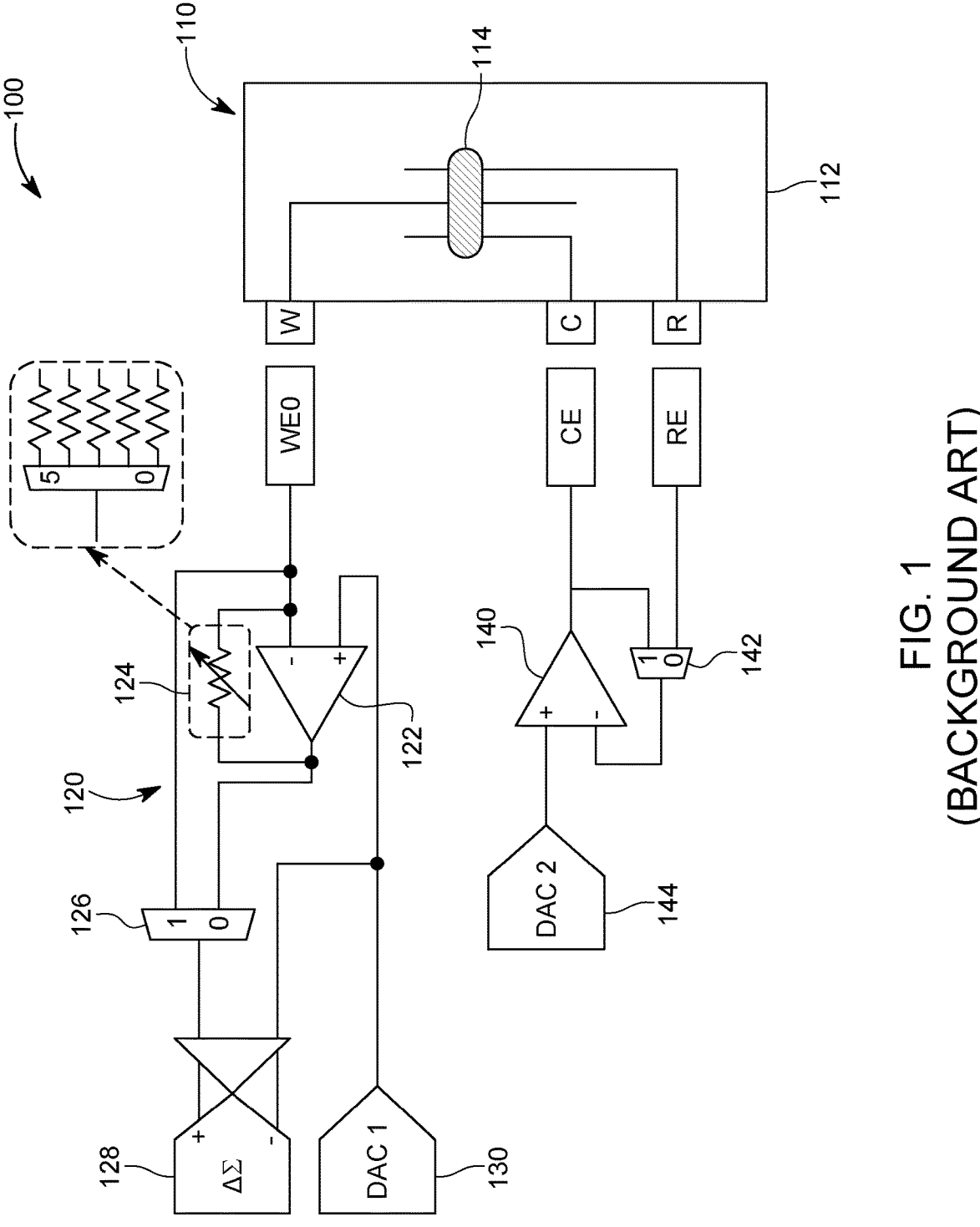
FIG. 1 is a schematic diagram of readout circuitry having three electrodes for reading a sensor also having three electrodes.
Figure 2:
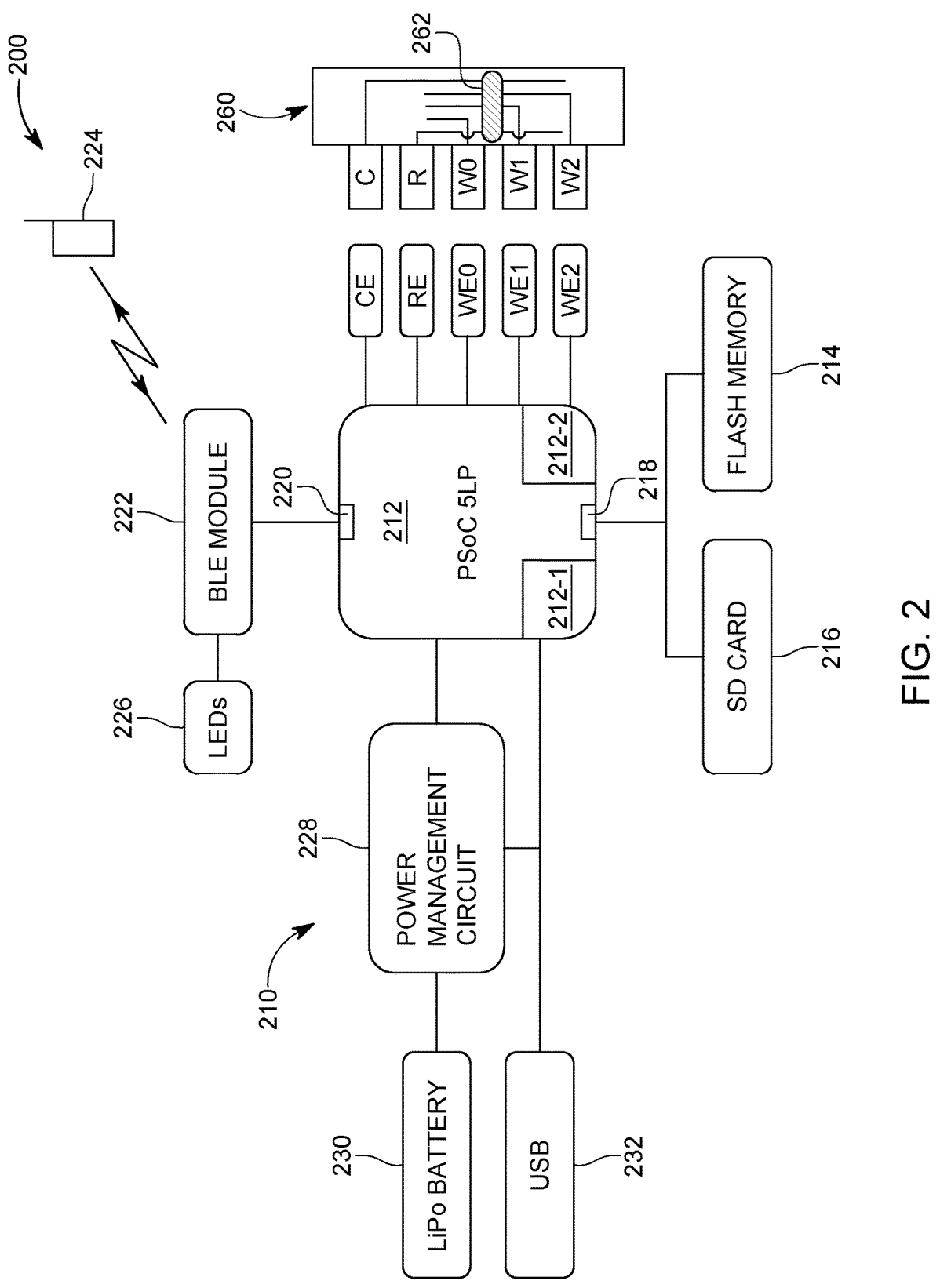
FIG. 2 is a schematic diagram of potentiostat circuitry for point of care testing.

FIG. 2 schematically illustrates some of the components of a potentiostat circuitry 210 having five electrode pads configured to be connected to 3, 4, or 5 corresponding electrodes of a cell/sensor 260. The potentiostat circuitry 210 together with the cell/sensor 260 form a POC testing device 200. The potentiostat circuitry 210 includes an integrated circuit 212, for example, a 32-bit Arm® Cortex®-M3 PSoC® 5LP (programmable system-on-chip from Cypress Semiconductor). Other integrated circuits may be used. The integrated circuit 212 includes, at a minimum, a processor 212-1 and a memory 212-2. It may include other elements, e.g., busses, controllers, gates, ports, etc. which are typically found in an integrated circuit. The integrated circuit 212 is electrically connected to the five electrode pads CE, RE, WE0, WE1, and WE2, which correspond to the counter electrode, reference electrode, first working electrode, second working electrode and third working electrode, respectively. The sensor 260 has corresponding electrodes C, R, W0, W1, and W2 for applying the desired voltages to the biological sample 262. The sensor 260 may be removably attach to the five electrode pads.

The integrated circuit 212 may also be connected to an external memory 214 and a memory card 216 through an interface 218, for example, through a serial peripheral interface (SPI). The external memory 214 may be flash memory and may be used to store the data collected from the sensor 260 or various procedures to be applied for each desired test. The integrated circuit 212 may also be connected to a communication unit 222, through another interface 220. The communication unit 222 may be, for example, a Bluetooth module, while the another interface 220 may be a universal asynchronous receiver-transmitter (UART) interface. Other interfaces may be used. The communication unit 222 may be used to exchange data or receive commands in a wireless manner with a server or base station, for example, a smart phone or smart device 224. One or more LED lights 226 may connected to the integrated circuit 212, either directly or through the communication module 222. Various modes or states of the potentiostat circuitry 210 may be signaled to a user with the LED, for example, if the command received by the integrated circuit 212 was not executed or understood, the LED may turn red, if the command was executed the LED may turn green, and if the command is being currently executed the LED may turn yellow. Other colors or flashing lights may be used to signal other states of the system.

The integrated circuit 212 is further connected to a power management circuit 228, which is configured to control the amount of power that is supplied to the integrated circuit, from what source, when to reduce the amount of power supplied etc. The structure of the power management circuit is known in the art and thus, its detailed structure is omitted herein. The power management circuit 228 is configured to control the power supplied either by a local battery 230 or by a given power port 232, e.g., a USB port. In one application, the potentiostat circuitry 210 is provided with its own battery 230, and thus, it is a standalone device that does not need the support of another device. However, if the size of the potentiostat circuitry 210 is of concern, to further reduce its footprint, it can be configured to receive its energy from the smart device 224, through the power port 232. In this case, the circuitry 210 does not have its own battery and it needs to be connected to the smart device to function.

Figure 3:
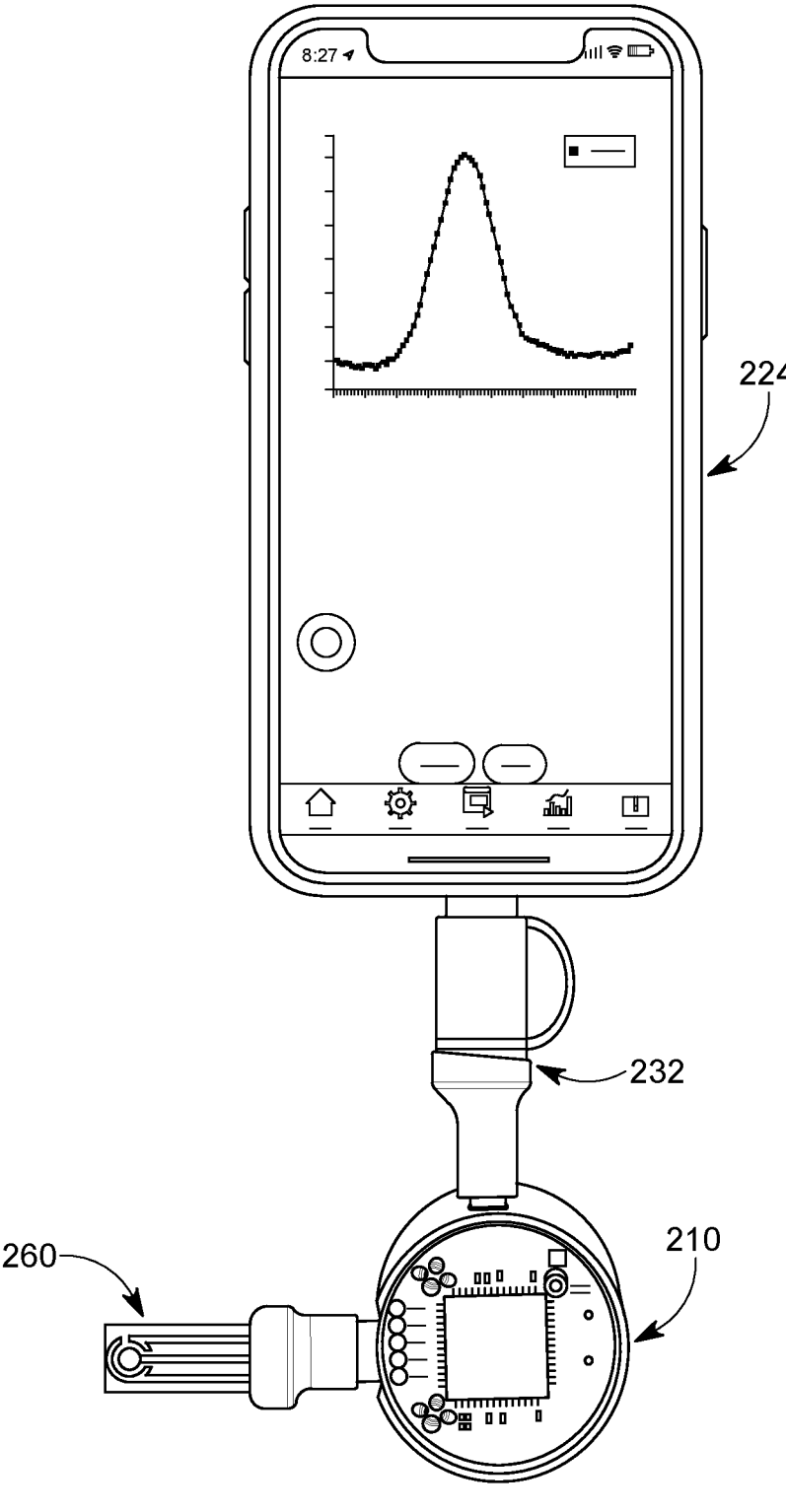
FIG. 3 illustrates the potentiostat circuitry of FIG. 2 being physically attached to a smartphone.
Figure 4:
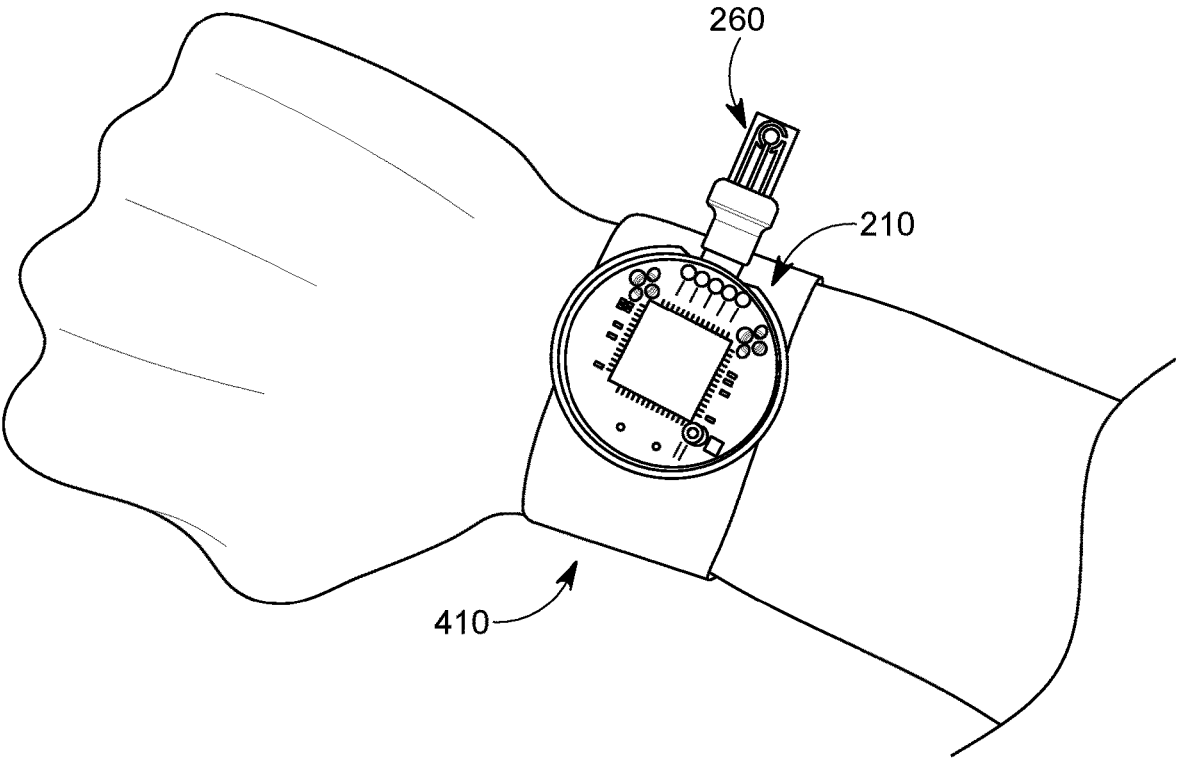
FIG. 4 illustrates the potentiostat circuitry of FIG. 2 being implemented as a portable wrist device.

For example, FIG. 3 shows the potentiostat circuitry 210 connected to the sensor 260 and the power port 232 connected to a smart phone 224 for supplying the necessary power. In another embodiment, as illustrated in FIG. 4, the potentiostat circuitry 210 is implemented as a standalone device, i.e., it has its own power source 230, and it attached to the wrist of a patient with a link 410. In one implementation, the embodiment of the potentiostat circuitry 210 shown in FIG. 4 may be merged into a smart watch so that the user of the smart watch does not need to take care of additional devices. If this integration is preferred, then the potentiostat circuitry 210 can be charged as a smart watch and all the communications between the potentiostat circuitry 210 and the smart device 224 is achieved through the smart watch.

Figure 5:
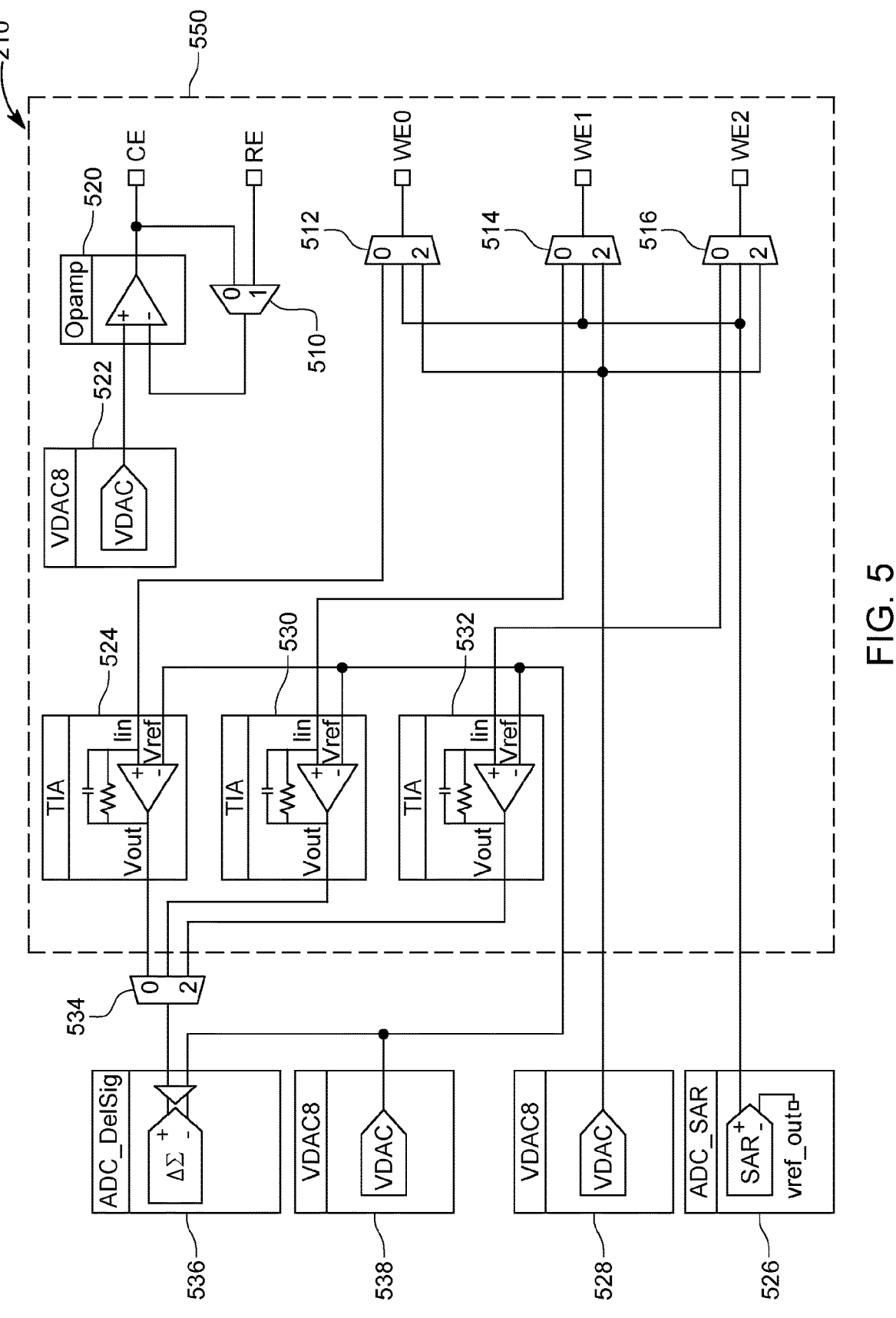
FIG. 5 illustrates in more detail various electronic components of the potentiostat circuitry of FIG. 2.

The potentiostat circuitry 210 uses plural multiplexer devices to reconfigure/change its circuit interface to match different applications, i.e., different sensors 260, the application of different voltages depending on the test to be performed, the number of electrodes that are active depending on the type of sensor 260, the number of tests to be simultaneously performed, etc. More specifically, as shown in FIG. 5, each of the five electrode pads CE, RE, WE0, WE1, and WE2 are connected to a corresponding multiplexer device 510, 512, 514, or 516. The multiplexer device 510 is a dual-state multiplexer while the other multiplexer devices 512, 514, and 516 are tri-state multiplexers. A dual-state multiplexer may be configured to select and implement one of two possible states, while a tri-state multiplexer may be configured to select and implement one of three possible states. Any state of the possible states may be selected and implemented in the potentiostat circuitry 210, for example, by the processor 212-1. For example, for a first test, the dual-state multiplexer device 510 may select a "0" state from the 0 and 1 possible states, the first tri-state multiplexer device 512 may select a "1" state from the 0, 1, and 2 possible states, the second tri-state multiplexer device 514 may select a "0" state from the 0, 1, and 2 possible states, and the third tri-state multiplexer device 516 may select a "2" state from the 0, 1, and 2 possible states. While the states noted above are exemplary, one skilled in the art would understand that the potentiostat circuitry 210 (e.g., the processor 212-1 in the integrated circuit 212) can be configured to select any combination of states for the multiplexer devices.

The dual-state multiplexer device 510 is connected to the counter electrode pad CE and to the reference electrode pad RE. When the state 0 is selected, the CE electrode pad is connected to the (output and one input) op-amp 520, while the RE electrode pad is floating. When the state 1 is selected, the situation is reversed, i.e., the CE is floating and the RE is connected to the input of the op-amp 520. The op-amp 520 is connected to a voltage digital-to-analog converter 522. All these elements are part of the potentiostat circuitry 210, and more specifically, part of the integrated circuit 212.

The first tri-state multiplexer device 512 is electrically connected to the first working electrode pad WE0. When the state 0 is selected, the first working electrode pad WE0 is electrically connected to a first transimpedance amplifier 524, which is a current to voltage converter. When the state 1 is selected, the first working electrode pad WE0 is electrically connected to a successive-approximation analog to digital converter 526, which is a converter that converts a continuous analog waveform into a discrete digital representation using a binary search through all possible quantization levels before finally converging upon a digital output for each conversion. When the state 2 is selected, the first working electrode pad WE0 is electrically connected to a voltage digital-to-analog converter 528.

Similarly, the second tri-state multiplexer device 514 has three states, 0, 1, and 2, and it is electrically connected to the second working electrode WE1. For state 0, the second working electrode WE1 is electrically connected, through the second tri-state multiplexer device 514, to a second transimpedance amplifier 530. For state 1, the second working electrode WE1 is electrically connected, through the second tri-state multiplexer device 514, to the successive-approximation analog to digital converter 526. For state 2, the second working electrode WE1 is electrically connected, through the second tri-state multiplexer device 514, to the voltage digital-to-analog converter 528.

The third tri-state multiplexer device 516 also has three states, 0, 1, and 2, and it is electrically connected to the third working electrode WE2. For state 0, the third working electrode WE2 is electrically connected, through the third tri-state multiplexer device 516, to a third transimpedance amplifier 532. For state 1, the third working electrode WE2 is electrically connected, through the third tri-state multiplexer device 516, to the successive-approximation analog to digital converter 526. For state 2, the third working electrode WE2 is electrically connected, through the third tri-state multiplexer device 516, to the voltage digital-to-analog converter 528. The five electrode pads CE, RE, WE0, WE1, and WE2 together with the corresponding converters 520, 524, 530, and 532 form a readout circuit 550.

The voltage outputs from the transimpedance amplifiers 524, 530, and 532 are electrically connected to a fourth tri-state multiplexer device 534. The fourth tri-state multiplexer device 534 electrically connects to a sigma-delta analog to digital converter $$\Delta \sum\nolimits_-^+ -ADC$$

536 so that for state 0, the first transimpedance amplifier 524 is connected to the converter 536, for state 1, the second transimpedance amplifier 530 is connected to the converter 536, and for state 2, the third transimpedance amplifier 532 is connected to the converter 536. The converter 536 is also electrically connected to a second voltage digital-to-analog converter 538 and provides a reference voltage for each of the transimpedance amplifiers 524, 530, and 532.

With this novel configuration, the potentiostat circuitry 210 can switch or reconfigure the electrode pads to perform tasks like measuring a voltage, or measuring a current, or applying a voltage, etc. Due to this configuration, the potentiostat circuitry 210 can simultaneously read up to three different electrodes, using the same reference and same counter electrodes. The potentiostat circuitry 210 can also change its impedance to control the current flow into the electrodes. This circuitry modification happens directly in the operational amplifier and feedback resistance, and it is complementary to the voltage potential applied into the electrodes. Table I illustrated in FIG. 6 presents the various combinations of simultaneous measurements that can be applied using this novel potentiostat circuitry 210. It is noted that seven measurement techniques can be achieved with the configuration of the new potentiostat circuitry 210, where Φ in the table stands for a two-electrode electrochemical cell, Π stands for a three-electrode electrochemical cell, and Θ stands for a five-electrode multiplexed electrochemical cell. In other words, if a two- or three-electrode cell or sensor 260 is used with the potentiostat circuitry 210, then two of such cells or sensors can be simultaneously connected to the electrode pads and simultaneously measured. However, if a five-electrode cell or sensor is attached to the potentiostat circuitry 210, only that cell or sensor can be connected to the electrode pads.

In one embodiment, the potentiostat circuitry 210 can be configured for higher voltage applications. Note that the battery 230 used with the potentiostat circuitry 210 provides about 3.7 V. If the potentiostat circuitry 210 is used with the power port 232, the voltage obtained from the smartphone 224 is about the same, i.e., 3.7 V. There are some POC tests that require a higher voltage, e.g., higher then +/−5V. For these applications, neither the battery nor the smart device can provide the required voltage. Thus, in this embodiment, a DC-to-DC up-converter module is added and this module is configured to increase the voltage from 3.7 V to about 14.8 V. The module is also configured to regulate this increased voltage to three different levels, e.g., +12V, +10V, and +5V. These levels are used to feed the output stage of the potentiostat circuitry 210. While the integrated circuit 212 of the potentiostat circuitry 210 is still powered by the low voltage supplied by the battery 230 or power port 232, a voltage conditioning circuit may be implemented to uplift the signal to enable the control of the readout circuitry at a higher voltage. The added module together with the potentiostat circuitry 210 creates a virtual ground relative to the voltage applied to the electrochemical cell, thus enabling the application of negative voltages.

Figure 7:
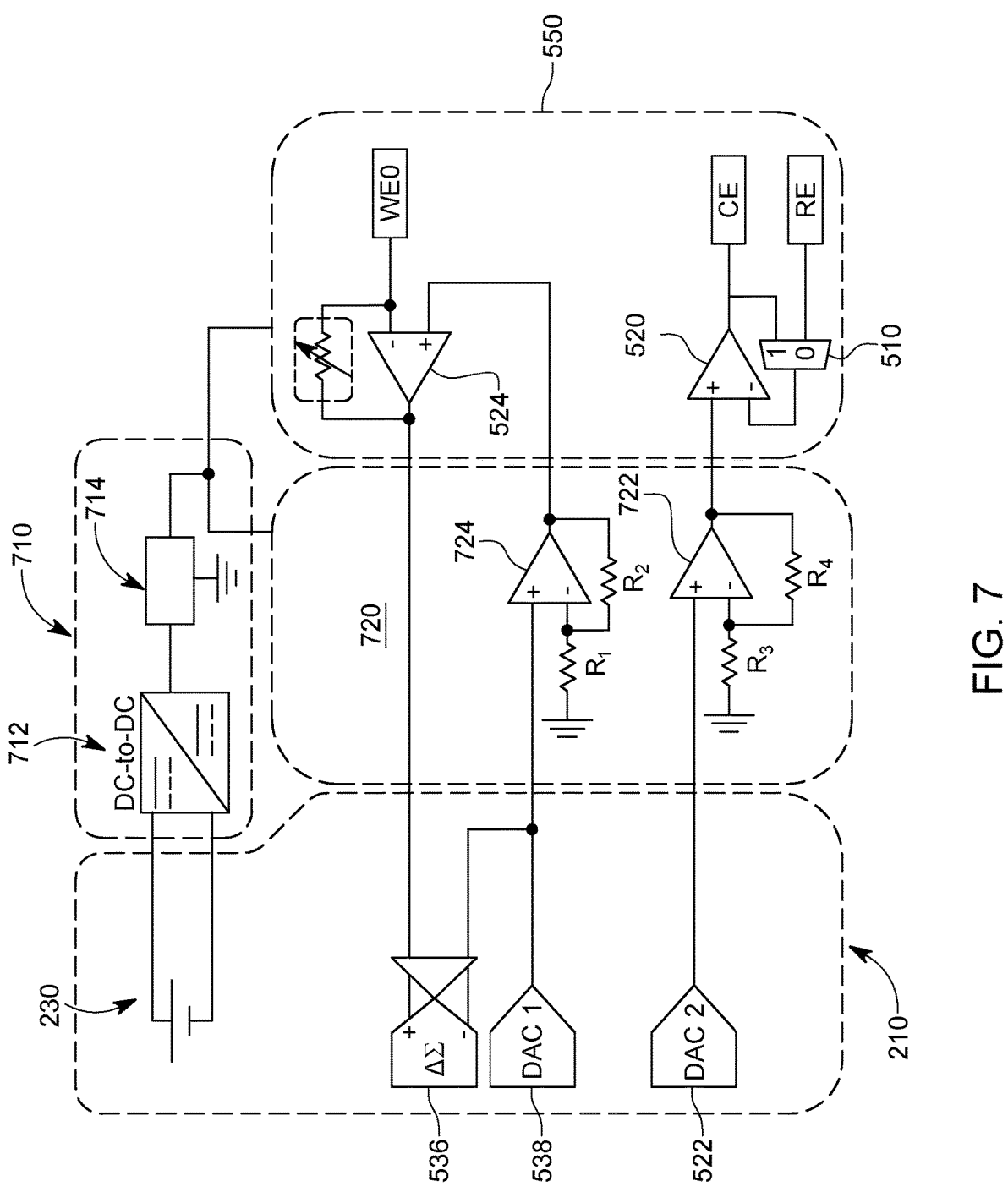
FIG. 7 illustrates a variation of the potentiostat circuitry that includes a voltage up-converter and a voltage conditioning circuit.

More specifically, as shown in FIG. 7, a DC-to-DC up-converter module 710 is electrically inserted between the power supply 230 of the potentiostat circuitry 210 and the readout circuit 550. Only one working electrode is shown in the figure for simplicity, but all three working electrodes may be present. The up-converter module 710 includes, at a minimum, a DC-to-DC transformer 712 and a voltage regulator 714, to ensure a steady voltage supply. The up-converter module 710 is electrically connected to a voltage conditioning circuit 720 and the readout circuit 550. The voltage conditioning circuit 720 is electrically connected to the converters 522, 536, and 538 of the potentiostat circuitry 210, and the voltage conditioning circuitry 720 includes operational amplifiers 722 and 724 connected with corresponding inputs to the digital-to-analog converters 522 and 538, respectively. The other inputs of the operational amplifiers 722 and 724 are connected to ground, via corresponding resistances R1 and R3. Resistances R2 and R4 connect these other inputs to the outputs of the amplifiers. The outputs of the amplifiers 722 and 724 are also connected to the input of the op-amps 520 and 524, respectively. Depending on the measurement configuration, i.e., bipolar or unipolar, the current range of the POC testing device 700 changes as illustrated in the table in FIG. 8.

Figure 9:
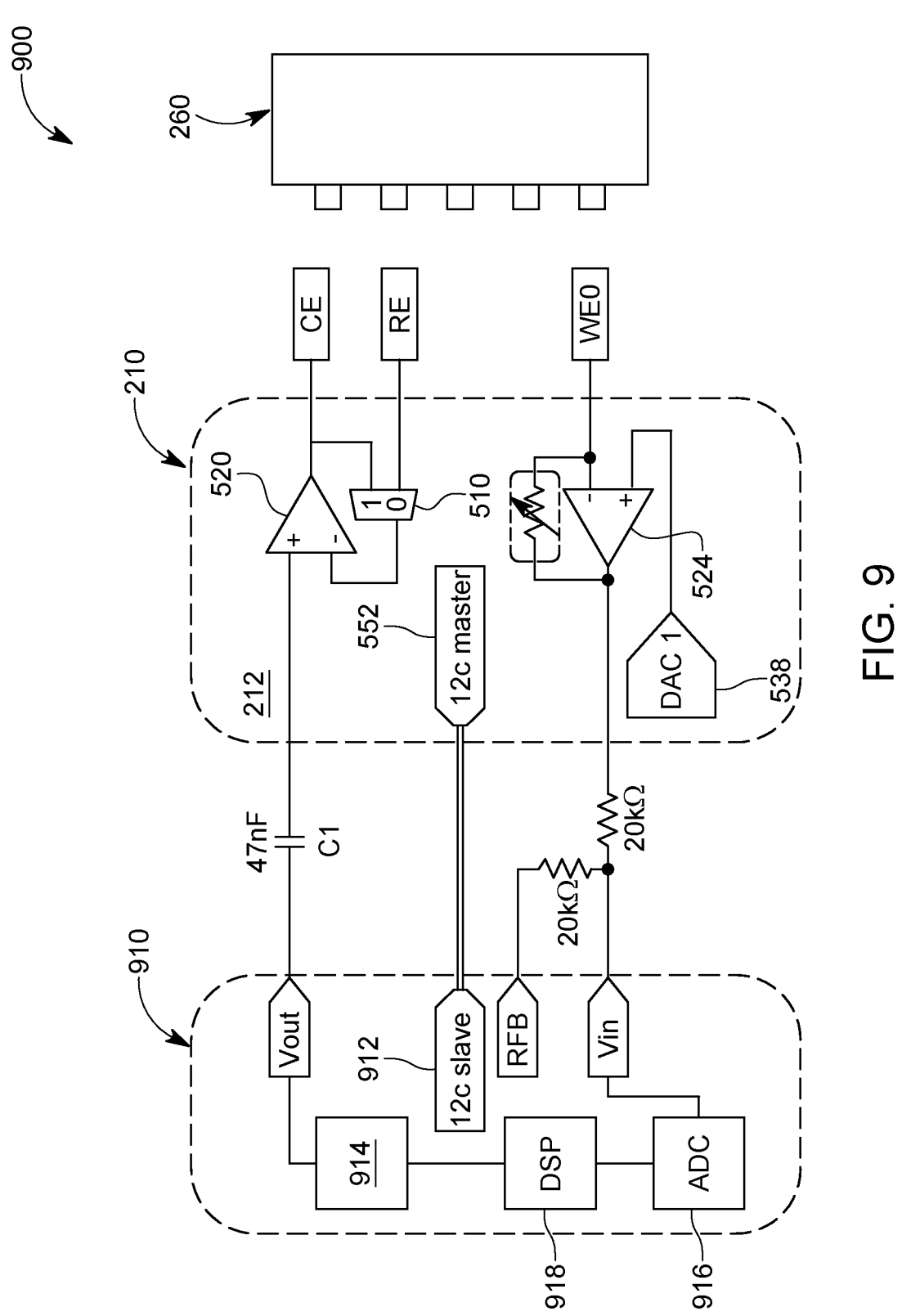
FIG. 9 illustrates another variation of the potentiostat circuitry that includes a frequency generator and digital signal processing for determining the impedance of a cell/sensor attached to the potentiostat circuitry.

Some of the POC tests require that an impedance of the biological material to be analyzed is measured. The potentiostat circuitry 210 is capable to also measure the impedance of such biological material by using the same electrode pads that are connected to the cell or sensor 260. This feature allows to perform common electrochemical techniques and impedance measurement without changing the connection with the sensor, just reconfiguring the electrical connections of the electrode pads to the various electronic components of the integrated circuit 212. More specifically, as shown in FIG. 9, a high-precision impedance converter system 910 (for example, system AD5933) that combines an on-board frequency generator with a 12-bit analog to digital converter is used to excite an exterior impedance (the sensor or cell 264) with a known frequency and the analog to digital converter samples the response signal from the impedance and determines the excitation frequency. The integrated circuit 212 is used as a front-end circuit and I²C master hub. I²C is known in the art to be an inter-integrated circuit bus used for attaching low speed peripherals to processors.

FIG. 9 shows the integrated circuit 212 and the master hub 552. The master hub 552 is electrically connected to a corresponding I²C slave of the impedance converter system 910. A frequency generator 914 allows the external complex impedance of the sensor or cell 260 to be excited with a known frequency. The response signal from the impedance 260 is sampled by the on-board ADC 916 and a discrete Fourier transform (DFT) is processed by an on-board digital signal processor (DSP) engine 918. A resistance RFB may be used in the impedance converter system 910 for measuring the impedance, and this resistance is electrically connected to a Vin terminal, which is electrically connected to the output of the op-amp 524. A Vout terminal is also present and is electrically connected, through a capacitor C1, to one input of the op-amp 520. The DFT algorithm run in the DSP engine 918 returns a real and imaginary data-word at each output frequency, which represents the measured impedance. The POC testing device 900 shown in FIG. 9 is thus capable of measuring impedances of the cell/sensor 260.

Figure 10A:
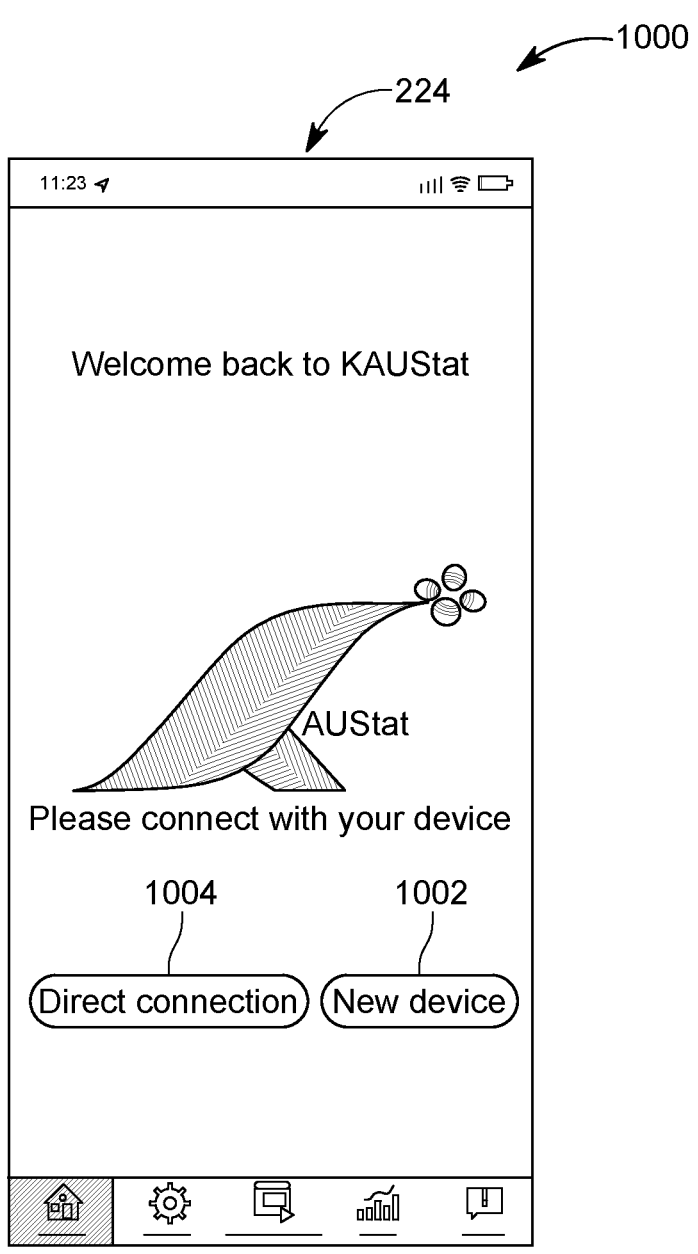
FIGS. 10A to 10D illustrate various screens generated by an application that uses the potentiostat circuitry to perform a point of care test.
Figure 10B:
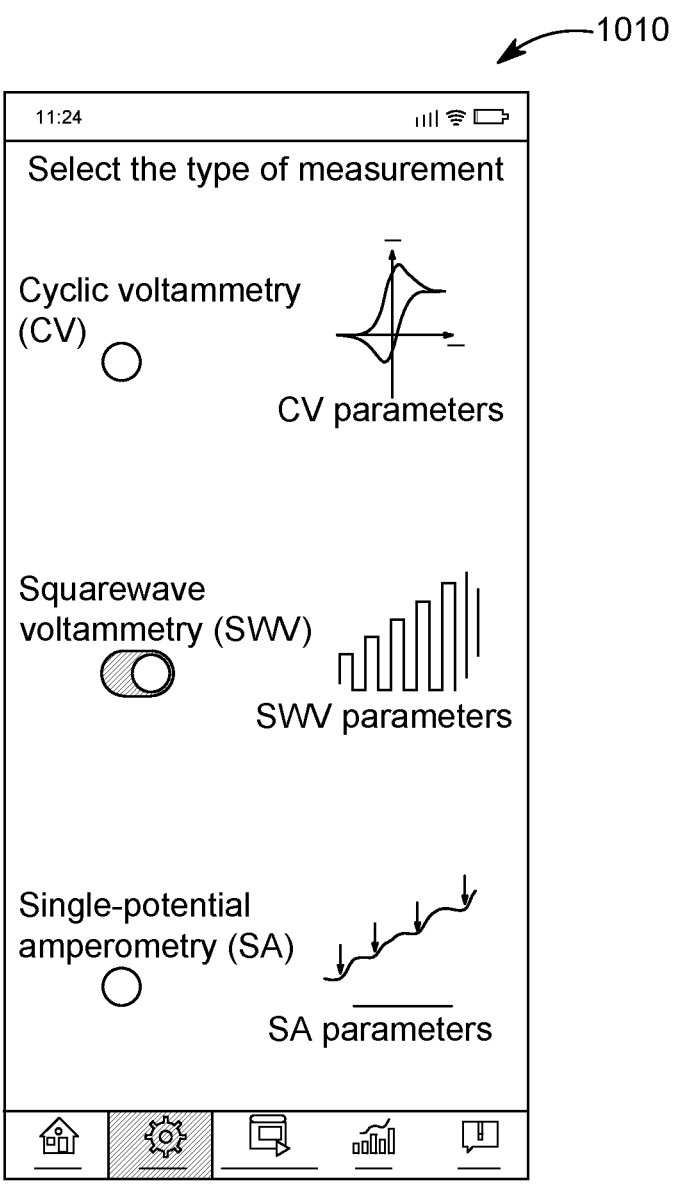
Figure 10C:
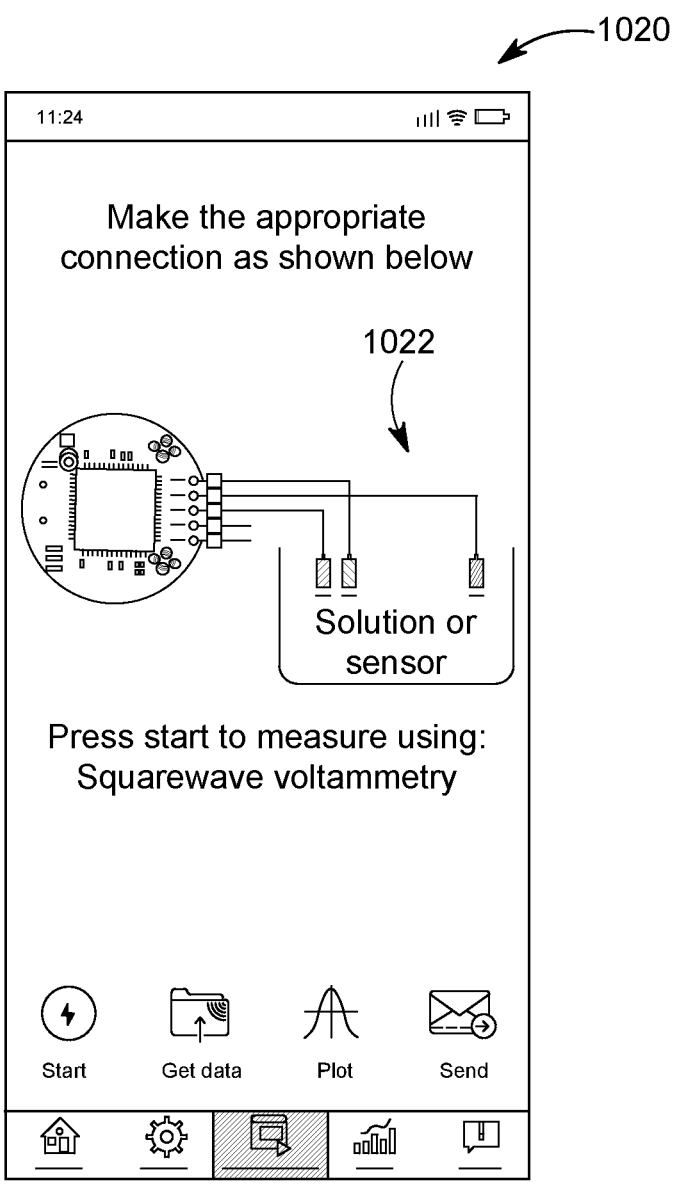
Figure 10D:
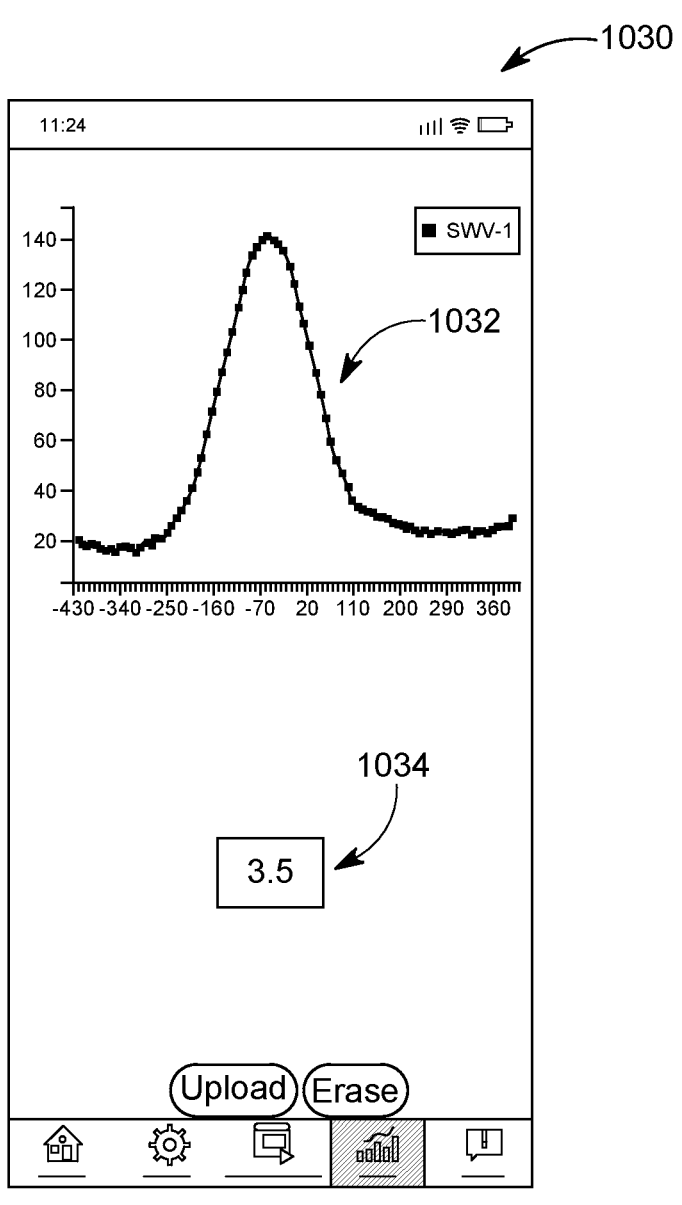
Figure 11:
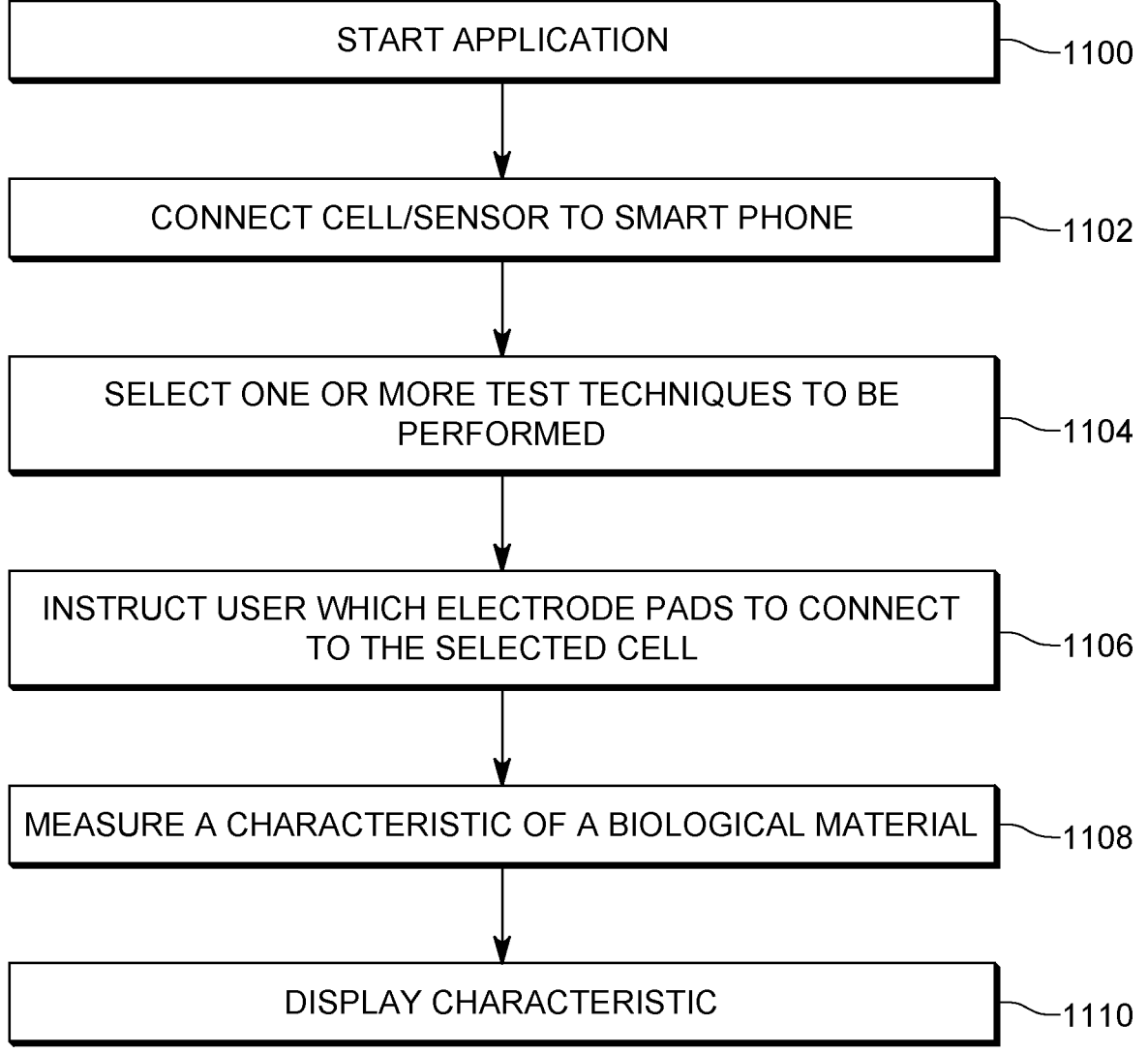
FIG. 11 is a flow chart of a method for performing a point of test care with the potentiostat circuitry.

An application for being used with the POC testing device 200, 700 and 900 discussed above is illustrated in FIGS. 10A to 10D and a method for performing one or more POC tests with such application is discussed with regard to FIG. 11. The application was designed to control the electrochemical techniques applied by the potentiostat circuitry and display the data graphically. The communication between the smartphone 224 and the potentiostat circuitry 210 was implemented through the Generic Attribute Profile (GATT) Bluetooth protocol. However, other protocols may be used.

After the application is launched in step 1100, FIG. 10A shows the welcome screen of the application 1000 on the smart phone 224. The welcome screen offers the user the option to wirelessly connect 1002 or to directly connect 1004 to a desired cell/sensor 260. Once the connection (wireless or wired) between the smart phone 224 and the cell/sensor 260 is achieved in step 1102, a new screen 1010 is presented to the user, as illustrated in FIG. 10B, and this new screen asks the user to select which method/technique to use. As previously discussed with regard to FIG. 6, plural test techniques may be used.

In step 1104, the user selects one or more techniques to be performed. Once the one or more test techniques have been selected, the application presents a new screen 1020, as shown in FIG. 10C, instructing the user in step 1106 to connect a cell/sensor 260 to the electrode pads of the potentiostat circuitry 210. In this step, the application may present not only written instructions for the user to be followed, but may also present pictorial sketches 1022 that indicate which electrode pad of the potentiostat circuitry should be connected to which electrode of the selected cell/sensor 260, as schematically illustrated in FIG. 10C. Note that due to the novel design of the potentiostat circuitry 210, the selected cell/sensor 260 may have between 3 to 5 electrodes and thus, in some circumstances, some of the electrode pads of the potentiostat circuitry are left floating. Once the connection between the electrode pads of the potentiostat circuitry and the cell/sensor is achieved, the application instructs the user to start the measuring phase. At this time, the potentiostat circuitry sends the appropriate current, or voltage, or frequency or a combination of them, and measures in step 1108 the response form the cell/sensor, which corresponds to a characteristic of the measured biological material, and the processed data is displayed in step 1110 on a new screen 1030, as shown in FIG. 10D.

In one embodiment, the measured characteristic may be displayed as a graph 1032, or as an absolute value 1034, for example, the A1c result for blood sugar when the biological material is blood. In this way, the user of the potentiostat circuitry is capable of performing various tests at home. The user may then change the selected cell/sensor with another one, or may simultaneously add two or three cell/sensors to the potentiostat circuitry to perform other tests. In this way, the user is spared the effort and cost of travelling to a specialized lab for performing these tests, and also his or her anguish to have these tests performed by another person in a non-familiar environment is reduced. The cell/sensor may be mailed by the specialized lab or by the medical provider of the user to his or her address and, after the completion of the tests, the cell/sensors may be disposed at the user's side.

The disclosed embodiments provide a small, reconfigurable multi-measurement testing device for point of care applications. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. Potentiostat circuitry for performing electrical tests on a biological material, the potentiostat circuitry comprising:
   an integrated circuit having a processor;
   a power source configured to supply power to the integrated circuit;
   a reference electrode pad (RE) electrically connected to the integrated circuit and configured to electrically connect to a reference electrode of a sensor;
   a counter electrode pad (CE) electrically connected to the integrated circuit and configured to electrically connect to a counter electrode of the sensor;
   a first working electrode pad (WE0) electrically connected to the integrated circuit and configured to electrically connect to a first working electrode of the sensor;
   a second working electrode pad (WE1) electrically connected to the integrated circuit and configured to electrically connect to a second working electrode of the sensor or to a first working electrode of another sensor;
   a third working electrode (WE2) pad electrically connected to the integrated circuit and configured to electrically connect to a third working electrode of the sensor or to a second working electrode of the another sensor;
   a wireless communication interface configured to exchange data and/or commands with a smart device; and
   a first tri-state multiplexer device electrically coupled between the first working electrode pad and plural internal circuit blocks of the integrated circuit,
   wherein the processor is configured to select one of three states for the first tri-state multiplexer device such that:
   in a first state 0, the first tri-state multiplexer device electrically connects the first working electrode pad to a first internal circuit block of the plural internal circuit blocks,
   in a second state 1, the first tri-state multiplexer device electrically connects the first working electrode pad to a second internal circuit block of the plural internal circuit blocks, and
   in a third state 2, the first tri-state multiplexer device electrically connects the first working electrode pad to a third internal circuit block of the plural internal circuit blocks.

2. The potentiostat circuitry of claim 1, further comprising:
   second and third tri-state multiplexer devices configured to connect the second working electrode pad and the third working electrode pad to the plural internal circuit blocks,
   wherein each of the second and third tri-state multiplexer devices has three distinct states.

3. The potentiostat circuitry of claim 2, wherein the processor of the integrated circuitry is configured to select a corresponding state of each of the second and third tri-state multiplexer devices.

4. The potentiostat circuitry of claim 3, wherein the first internal circuit block is a first transimpedance amplifier, the second internal circuit block is an analog to digital converter, and the third internal circuit block is a voltage digital-to-analog converter.

5. The potentiostat circuitry of claim 4, wherein for a first state 0, the second tri-state multiplexer device electrically connects the second working electrode pad to a second transimpedance amplifier, for a second state 1, the second tri-state multiplexer device electrically connects the second working electrode pad to the analog to digital converter, and for a third state 2, the second tri-state multiplexer device electrically connects the second working electrode pad to the voltage digital-to-analog converter.

6. The potentiostat circuitry of claim 5, wherein for a first state 0, the third tri-state multiplexer device electrically connects the third working electrode pad to a third transimpedance amplifier, for a second state 1, the third tri-state multiplexer device electrically connects the third working electrode pad to the analog to digital converter, and for a third state 2, the third tri-state multiplexer device electrically connects the third working electrode pad to the voltage digital-to-analog converter.

7. The potentiostat circuitry of claim 6, further comprising:
a fourth tri-state multiplexer device that is configured to connect a selected output of the first to third transimpedance amplifiers to a sigma-delta analog-to-digital converter.

8. The potentiostat circuitry of claim 7, wherein the processor of the integrated circuitry is configured to select one of the first to third states for each of the first to fourth tri-state multiplexer devices based on a test to be performed.

9. The potentiostat circuitry of claim 8, further comprising:
a first operational amplifier; and
a dual-state multiplexer device that electrically connects the reference electrode pad and the counter electrode pad to an input the first operational amplifier.

10. The potentiostat circuitry of claim 6, further comprising:
a voltage up-converter module connected to the power source and configured to increase a voltage generated by the power source; and
a voltage conditioning circuit electrically connected to the first to third transimpedance amplifiers.

11. The potentiostat circuitry of claim 6, further comprising:
an impedance converter circuit electrically connected to the integrated circuit through an inter-integrated circuit bus.

12. The potentiostat circuitry of claim 11, wherein the impedance converter circuit comprises:
a frequency generator unit that generates a frequency for exciting the sensor; and
a digital signal processor configured to analyze a received frequency and determine an impedance of the biological material.

13. A point of contact testing device for determining a characteristic of a biological material, the point of contact testing device comprising:
a sensor having a reference electrode (R), a counter electrode (C), and at least one working electrode (W1), the sensor being configured to receive the biological material; and
potentiostat circuitry including,
an integrated circuit having a processor, a reference electrode pad (RE) electrically connected to the integrated circuit and configured to electrically connect to the reference electrode (R) of the sensor,
a counter electrode pad (CE) electrically connected to the integrated circuit and configured to electrically connect to the counter electrode (C) of the sensor,
a first working electrode pad (WE0) electrically connected to the integrated circuit and configured to electrically connect to the first working electrode (W1) of the sensor,
a second working electrode pad (WE1) electrically connected to the integrated circuit and configured to electrically connect to a second working electrode of the sensor or to a first working electrode of another sensor,
a third working electrode pad (WE2) electrically connected to the integrated circuit and configured to electrically connect to a third working electrode of the sensor or to a second working electrode of the another sensor,
a wireless communication interface configured to exchange data and/or commands with a smart device,
a first tri-state multiplexer device electrically coupled between the first working electrode pad and plural internal circuit blocks of the integrated circuit,
wherein the processor is configured to select one of three states for the first tri-state multiplexer device such that:
in a first state 0, the first tri-state multiplexer device electrically connects the first working electrode pad to a first internal circuit block of the plural internal circuit blocks,
in a second state 1, the first tri-state multiplexer device electrically connects the first working electrode pad to a second internal circuit block of the plural internal circuit blocks, and
in a third state 2, the first tri-state multiplexer device electrically connects the first working electrode pad to a third internal circuit block of the plural internal circuit blocks.

14. The point of contact testing device of claim 13, further comprising:
second and third tri-state multiplexer devices configured to connect the second working electrode pad and the third working electrode pad to the plural internal circuit blocks,
wherein each of the second and third tri-state multiplexer devices has three distinct states.

15. The point of contact testing device of claim 14, wherein the processor of the integrated circuitry is configured to select a corresponding state of each of the second and third tri-state multiplexer device.

16. The point of contact testing device of claim 15, wherein the first internal circuit block is a first transimpedance amplifier, the second internal circuit block is an analog to digital converter, and the third internal circuit board is a voltage digital-to-analog converter.

17. The point of contact testing device of claim 16, wherein for a first state 0, the second tri-state multiplexer device electrically connects the second working electrode pad to a second transimpedance amplifier, for a second state 1, the second tri-state multiplexer device electrically connects the second working electrode pad to the analog to digital converter, and for a third state 2, the second tri-state multiplexer device electrically connects the second working electrode pad to the voltage digital-to-analog converter.

18. The point of contact testing device of claim 17, wherein for a first state 0, the third tri-state multiplexer device electrically connects the third working electrode pad to a third transimpedance amplifier, for a second state 1, the third tri-state multiplexer device electrically connects the third working electrode pad to the analog to digital converter, and for a third state 2, the third tri-state multiplexer device electrically connects the third working electrode pad to the voltage digital-to-analog converter.

19. The point of contact testing device of claim 13, wherein the sensor includes three working electrodes.

20. The point of contact testing device of claim 13, wherein the sensor includes three electrodes and the another sensor also includes three electrodes and the potentiostat circuitry is configured to simultaneously connect to both the sensor and the another sensor.

* * * * *